(12) United States Patent
Sakai et al.

(10) Patent No.: US 11,172,812 B2
(45) Date of Patent: Nov. 16, 2021

(54) ENDOSCOPE

(71) Applicant: OLYMPUS CORPORATION, Tokyo (JP)

(72) Inventors: Youhei Sakai, Ina (JP); Keiichi Kobayashi, Sagamihara (JP); Yusuke Nakagawa, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 138 days.

(21) Appl. No.: 16/568,399

(22) Filed: Sep. 12, 2019

(65) Prior Publication Data

US 2020/0000328 A1 Jan. 2, 2020

Related U.S. Application Data

(63) Continuation of application No. PCT/JP2017/032479, filed on Sep. 8, 2017.

(30) Foreign Application Priority Data

Mar. 24, 2017 (WO) .................. PCT/JP2017/012048

(51) Int. Cl.
*A61B 1/05* (2006.01)
*A61B 1/00* (2006.01)

(52) U.S. Cl.
CPC .......... *A61B 1/051* (2013.01); *A61B 1/00013* (2013.01); *A61B 1/00018* (2013.01); *A61B 1/00124* (2013.01); *A61B 1/00126* (2013.01)

(58) Field of Classification Search
CPC ............ A61B 1/00013; A61B 1/00018; A61B 1/00124; A61B 1/00126; A61B 1/051
See application file for complete search history.

(56) References Cited

U.S. PATENT DOCUMENTS 9,810,898 B2 * 11/2017 Tomatsu ................ A61B 1/045
2010/0261961 A1 * 10/2010 Scott .................. G02B 23/2415
600/111

(Continued)

FOREIGN PATENT DOCUMENTS

EP 2624304 A1 8/2013
EP 2947486 A1 11/2015

(Continued)

OTHER PUBLICATIONS

International Search Report dated Nov. 21, 2017 issued in PCT/JP2017/032479.

*Primary Examiner* — Aaron B Fairchild
(74) *Attorney, Agent, or Firm* — Scully, Scott, Murphy & Presser, P.C.

(57) ABSTRACT

An endoscope includes an opto-electric composite module, an optical fiber, and a plurality of electric cables each including a core wire and a shielding wire. The opto-electric composite module includes a light emitting device, a wiring board including a plurality of bonding electrodes to which the plurality of core wires are bonded, a ferrule causing the optical fiber inserted into a first through hole to be optically coupled to the light emitting device, and a cable holder having grooves to which the plurality of core wires are fixed with the plurality of core wires so disposed as to be bonded to the plurality of respective bonding electrodes. The cable holder is a holder conductor electrically connected to a ground potential electrode of the image pickup device, and the shielding wires in the electric cables are bonded to the holder conductor of the cable holder via an electrically conductive member.

8 Claims, 14 Drawing Sheets

(56) References Cited

U.S. PATENT DOCUMENTS

| | | |
|---|---|---|
| 2013/0182099 A1 | 7/2013 | Nakamura |
| 2015/0318924 A1 | 11/2015 | Motohara |
| 2015/0335230 A1 | 11/2015 | Tomatsu |
| 2015/0342530 A1 | 12/2015 | Dekker et al. |
| 2016/0313552 A1 | 10/2016 | Tomatsu |
| 2017/0332888 A1* | 11/2017 | Amling ............... H04N 5/23241 |
| 2018/0008132 A1* | 1/2018 | Sakai ................. A61B 1/00013 |

FOREIGN PATENT DOCUMENTS

| | | |
|---|---|---|
| EP | 2954835 A1 | 12/2015 |
| EP | 3020324 A2 | 5/2016 |
| JP | 2010-40214 A | 2/2010 |
| JP | 2012-079851 A | 4/2012 |
| JP | 2012-183330 A | 9/2012 |
| JP | 2014-038272 A | 2/2014 |
| JP | 2014-137584 A | 7/2014 |
| JP | 2015-029774 A | 2/2015 |
| JP | 2015-068835 A | 4/2015 |
| JP | 2015-134039 A | 7/2015 |
| JP | 2015-524285 A | 8/2015 |
| JP | 2016-194601 A | 11/2016 |
| WO | WO 2012/043187 A1 | 4/2012 |
| WO | WO 2014/006536 A2 | 1/2014 |
| WO | WO 2014/112461 A1 | 7/2014 |
| WO | WO 2015/107852 A1 | 7/2015 |
| WO | WO 2017/109930 A1 | 6/2017 |

\* cited by examiner

ENDOSCOPE

CROSS REFERENCE TO RELATED APPLICATION

This application is a continuation application of PCT/JP2017/032479 filed on Sep. 8, 2017 and claims benefit of PCT/JP2017/012048 filed on Mar. 24, 2017, the entire contents of which are incorporated herein by this reference.

BACKGROUND OF INVENTION

1. Field of the Invention

The present invention relates to an endoscope in which an opto-electric composite module including an optical transmission module and an opto-electric composite cable is disposed in a distal end portion of an insertion portion.

2. Description of the Related Art

An endoscope includes an image pickup portion, such as a CCD, at a distal end portion of an elongated insertion portion. In recent years, to display a high-quality image, an image pickup portion having a large number of pixels has been studied. Using an image pickup portion having a large number of pixels increases the amount of image signal transmitted from the image pickup portion to a signal processing device (processor). Therefore, in electrical signal transmission along metal wiring, the insertion portion could undesirably be thick due to the metal wiring.

To reduce a diameter of the insertion portion for a small degree of invasion, it is preferable to employ optical signal transmission along a thin optical fiber using an optical signal in place of an electric signal. An optical transmission module configured to perform the optical signal transmission uses an E/O optical transmission module configured to convert an electric signal into an optical signal (electro-optical converter), an O/E optical transmission module configured to convert an optical signal into an electric signal (opto-electric converter), and an optical fiber. An electric cable configured to transmit an electric signal is connected to the optical transmission module.

Japanese Patent Application Laid-Open Publication No. 2015-134039 discloses an opto-electric composite module in which an opto-electric composite cable including an optical fiber and an electric cable is connected to an optical module. The optical fiber is so disposed as to be optically coupled to a photoelectric conversion device mounted on a first printed board, and the electric cable is bonded to a second printed board.

Japanese Patent Application Laid-Open Publication No. 2010-40214 discloses a grounding member configured to place and fix a plurality of coaxial cables in predetermined positions and connects shield wires of the coaxial cables to a common ground.

SUMMARY OF THE INVENTION

An endoscope according to an embodiment of the present invention is an endoscope including an opto-electric composite module disposed in a distal end portion of an insertion portion and configured to convert an electric signal into an optical signal, an optical fiber inserted through the insertion portion and configured to transmit the optical signal, and a plurality of electric cables inserted through the insertion portion and each include a core wire and a shielding wire. The opto-electric composite module includes: an image pickup device; a light emitting device configured to convert the electric signal outputted by the image pickup device into the optical signal; a wiring board having a first principal surface and a second principal surface, with the light emitting device mounted on the first principal surface, and including a plurality of bonding electrodes to which the plurality of core wires are bonded, respectively; a ferrule having a first through hole, with the optical fiber inserted into the first through hole optically coupled to the light emitting device; and a cable holder having a plurality of grooves or holes to which the plurality of core wires are fixed with the plurality of core wires disposed in positions where the plurality of core wires are bonded to the plurality of respective bonding electrodes, the cable holder disposed in a position closer to the second principal surface than to the first principal surface of the wiring board. A surface of each of the plurality of grooves or a surface of each of the plurality of holes is a holder conductor electrically connected to a ground potential electrode of the image pickup device, and the shielding wires are bonded to the holder conductor of the cable holder via an electrically conductive member.

An endoscope according to another embodiment is an endoscope including an opto-electric composite module disposed in a distal end portion of an insertion portion, an optical fiber inserted through the insertion portion and configured to transmit an optical signal, and a plurality of electric cables inserted through the insertion portion and each include a core wire and a shielding wire. The opto-electric composite module includes: an image pickup device; a light emitting device configured to convert the electric signal outputted by the image pickup device into the optical signal; a wiring board having a first principal surface and a second principal surface, with the light emitting device mounted on the first principal surface, and including a plurality of bonding electrodes to which the plurality of core wires are bonded, respectively; and a ferrule having a first through hole, with the optical fiber inserted into the first through hole optically coupled to the light emitting device. A surface of the ferrule is a ferrule conductor electrically connected to a ground potential electrode of the image pickup device. The shielding wires in the electric cables are bonded to the ferrule conductor via an electrically conductive member.

DETAILED DESCRIPTION OF THE PREFERRED EMBODIMENTS

First Embodiment

Figure 1:
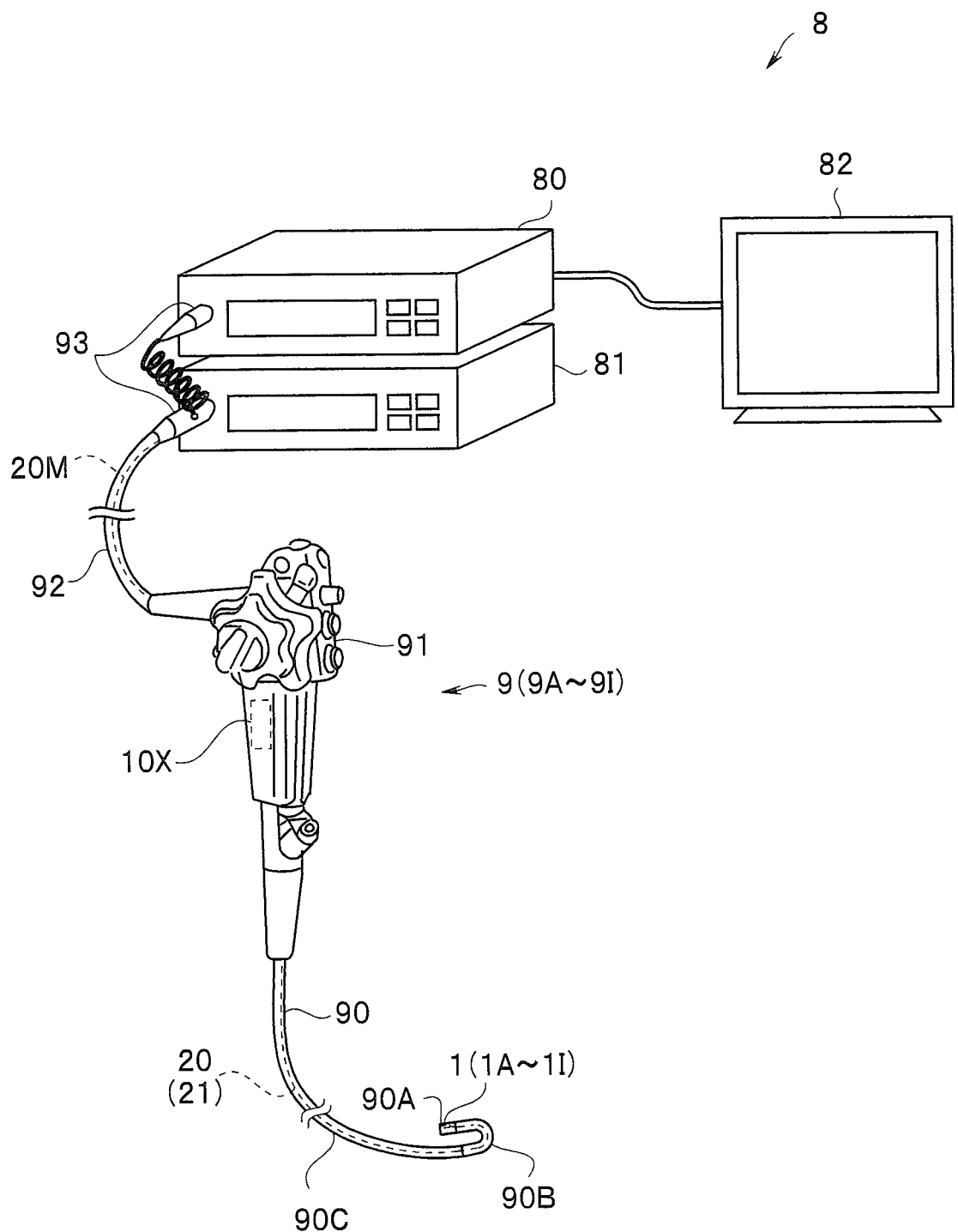
FIG. 1 is a configuration diagram of an endoscope system including an endoscope according to a first embodiment.

An endoscope system 8 including an endoscope 9 according to the present embodiment includes the endoscope 9, a processor 80, a light source apparatus 81, and a monitor 82, as shown in FIG. 1. The endoscope 9 includes an insertion portion 90, an operation portion 91, and a universal cord 92. The endoscope 9 operates as follows: the insertion portion 90 is inserted into, for example, a body cavity of an object; picks up an image of the interior of the body of the object; and outputs an image signal.

The insertion portion 90 is formed of a distal end portion 90A, which is part of the insertion portion 90 and in which an opto-electric composite module 1 including an E/O optical transmission module 10 (see FIG. 2) is disposed, a bendable bending portion 90B, which is continuously connected to a proximal end portion of the distal end portion 90A, and a flexible portion 90C, which is continuously connected to a proximal end portion of the bending portion 90B. The bending portion 90B bends in accordance with operation performed on the operation portion 91. The endoscope 9 may be a rigid endoscope or may be an endoscope for medical or industrial purposes.

The operation portion 91, on which a variety of buttons configured to operate the endoscope 9 are provided, is disposed at a proximal end portion of the insertion portion 90 of the endoscope 9. An O/E light receiving module 10X configured to convert an optical signal transmitted along an optical fiber 21 in an opto-electric composite cable 20 of the opto-electric composite module 1 into an electric signal is disposed in the operation portion 91.

The universal cord 92, which extends from the operation portion 91, is connected to the processor 80 and the light source apparatus 81 via a connector 93. The universal cord 92 allows insertion of an electric cable 20M configured to transmit the electric signal outputted from the O/E light receiving module 10X.

The processor 80 controls the entire endoscope system 8, performs signal processing on the electric signal outputted by the opto-electric composite module 1, and outputs the processed electric signal as an image signal. The monitor 82 displays the image signal outputted by the processor 80.

The light source apparatus 81 includes an LED light source formed, for example, of a white LED. Illumination light outputted by the light source apparatus 81 is guided to the distal end portion 90A via a light guide (not shown) inserted through the universal cord 92 and the insertion portion 90, and the illumination light then illuminates the object.

In the endoscope 9, an image pickup signal that is an electric signal outputted by the image pickup portion 40 (see FIG. 2), which is an image pickup device, is converted by the optical transmission module 10 in the distal end portion 90A into an optical signal, and optical signal is transmitted to the operation portion 9 via the thin optical fiber 21 in the opto-electric composite cable 20 inserted through the insertion portion 90. The optical signal is then converted by the O/E light receiving module 10X disposed in the operation portion 91 into an electric signal again, and the electric signal is transmitted to the electric connector 93 via the electric cable 20M which is metal wiring inserted through the universal cord 92 allows insertion.

In the insertion portion 90, the image pickup signal is transmitted via the small-diameter optical fiber 21, whereas in the universal cord 92, an outer diameter of which is not greatly restricted because the universal cord 92 is not inserted into the body, the image pickup signal is transmitted along the electric cable 20M, which is metal wiring thicker than the optical fiber 21. The small diameter of the insertion portion 90 makes the endoscope 9 less invasive.

In a case where the light receiving module 10X is disposed in the connector 93 or the processor 80, the universal cord 92 allows insertion of the opto-electric composite cable 20 (optical fiber 21).

Further, as described later, the opto-electric composite module 1 is an ultracompact module dedicated for endoscope and is highly reliable, whereby the endoscope 9 is highly reliable, compact (less invasive), and is readily manufactured.

Second Embodiment

Figure 2:
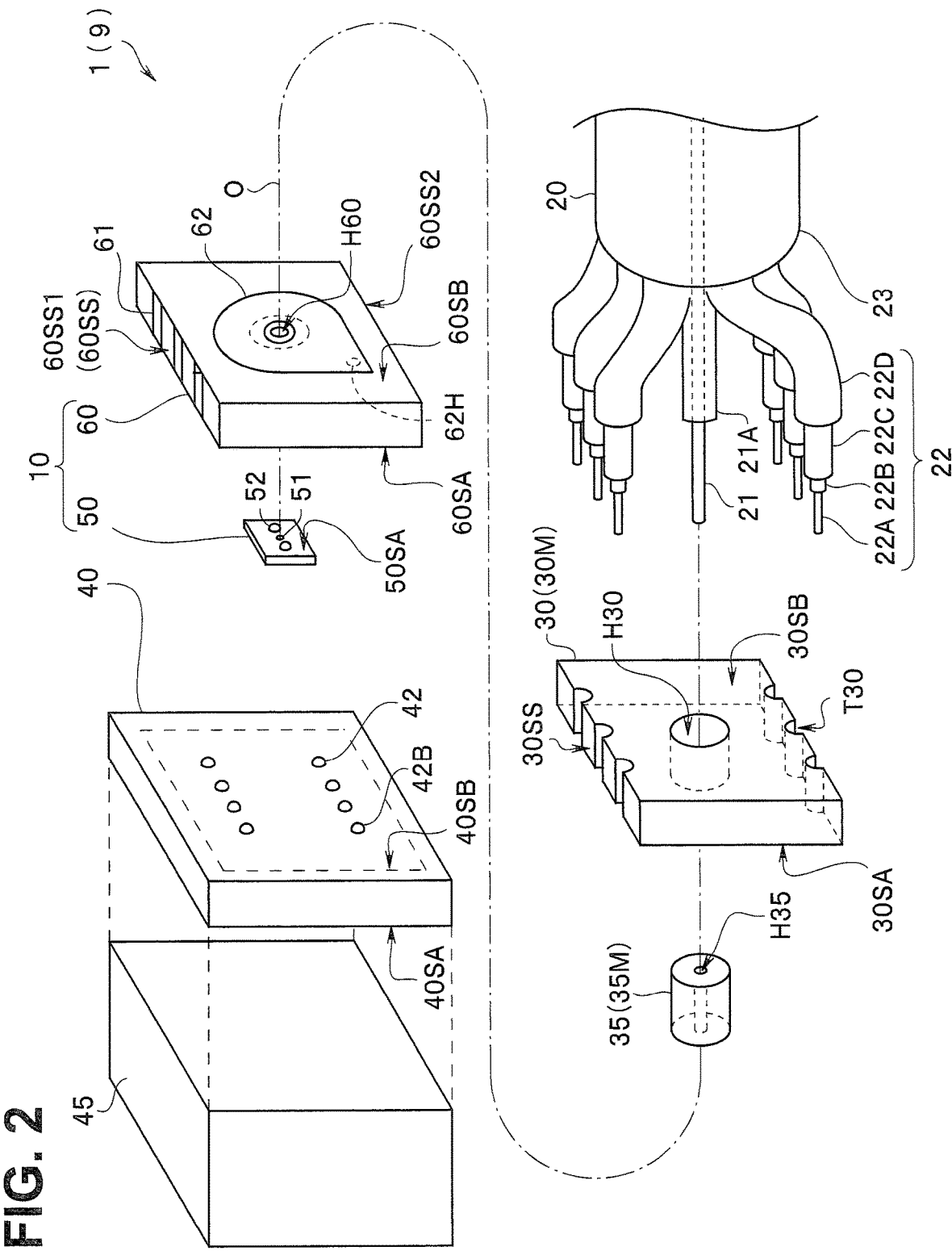
FIG. 2 is an exploded view of an opto-electric composite module of the endoscope according to a second embodiment.
Figure 3:
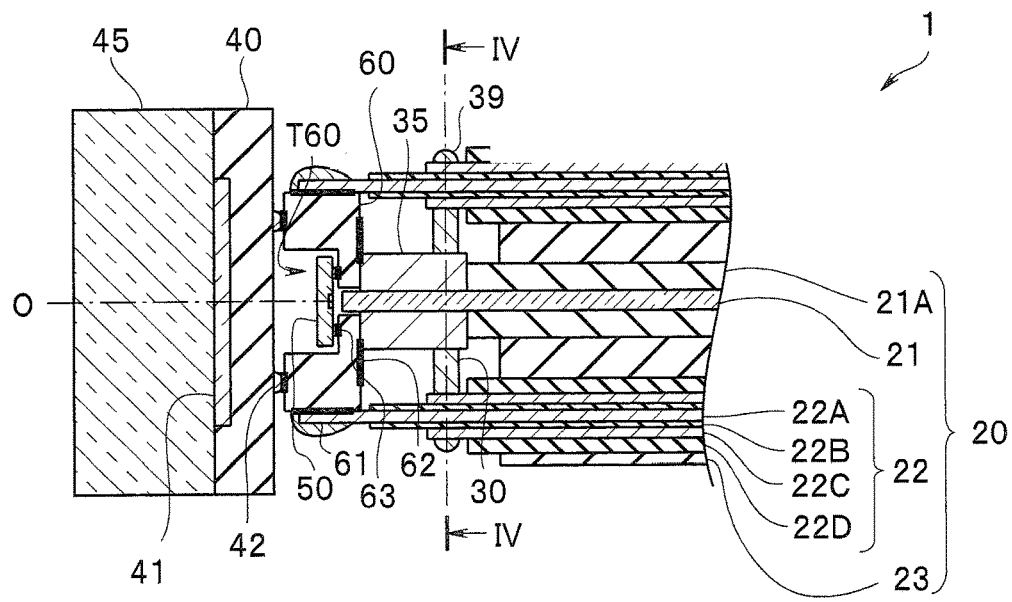
FIG. 3 is a cross-sectional view of the opto-electric composite module of the endoscope according to the second embodiment.
Figure 4:
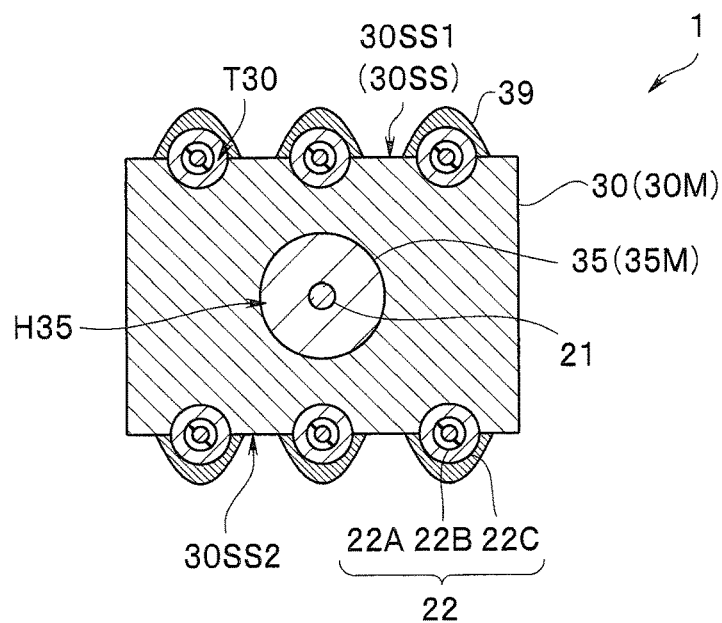
FIG. 4 is a cross-sectional view of the opto-electric composite module of the endoscope according to the second embodiment taken along the line IV-IV in FIG. 3.

The opto-electric composite module 1 in the present embodiment includes the optical transmission module 10, the opto-electric composite cable 20, and a cable holder 30, which is a cable holding portion as shown in FIGS. 2 to 4.

In the following description, note that the drawings based on each embodiment are each a schematic view, and that the relationship between the thickness and the width of each portion, the thickness ratio among portions, and other factors differ from the actual relationship, ratio, and other factors, and a portion in a drawing may differ from the same portion in another drawing in terms of the dimensional and the ratio in some cases. Further, part of the components is not shown, or no reference character is given to part of the components in some cases.

A light receiving portion 41 is formed on a light receiving surface 40SA of the image pickup portion 40, and the image pickup portion 40 picks up an image of an object and outputs an image pickup signal. External electrodes 42, which are connected to the light receiving portion 41, for example, via through wiring (not shown), are disposed on a rear surface 40SB, which faces the light receiving surface 40SA. Any of the plurality of external electrodes 42 of the image pickup portion 40 is a ground potential electrode 42B, which has ground potential.

A cover glass plate 45 is disposed on the light receiving surface 40SA of the image pickup portion 40. The image pickup portion 40 may be an image pickup device itself made of a semiconductor or an image pickup device with a wiring board and another semiconductor device bonded to a rear surface of the image pickup device.

A light emitting device 50 includes a light emitting portion 51, which converts the image pickup signal outputted by the image pickup portion 40 into an optical signal. For example, an ultracompact light emitting device 50, which has a dimension of 250 μm×250 μm in a plan view, has a light emitting surface 50SA, on which the light emitting portion 51 having a diameter of 10 μm and external electrodes 52, which supply the light emitting portion 51 with a drive signal, are provided.

A wiring board 60 has a roughly rectangular parallelpiped shape having a first principal surface 60SA, a second principal surface 60SB, and four side surfaces 60SS. The first principal surface 60SA has a recessed portion T60, and the external electrodes 52 of the light emitting device 50 is bonded to electrodes 63 on the bottom surface of the recessed portion T60. The wiring board 60 may be formed of a plurality of wiring boards or may be a molded interconnect device (MID).

The wiring board 60 has a hole portion H60, which serves as an optical path, in such a way that the hole portion H60 faces the light emitting portion 51 of the light emitting device 50. In a case where the wiring board 60 is formed of a base body that transmits light configured to carry the optical signal, the hole portion H60, which serves as an optical path, is not required.

An electrical conductor pattern 62, which is formed, for example, of a copper film, is disposed on the second principal surface 60SB of the wiring board 60. The electrical conductor pattern 62 is electrically connected to an electrode (not shown) on the first principal surface 60SA via through wiring 62H. The electrode on the first principal surface 60SA is bonded to the ground potential electrode 42B of the image pickup portion 40. In other words, the electrical conductor pattern 62 is a ground potential electrode on the wiring board 60. The electrical conductor pattern 62 on the second principal surface 60SB may be connected to the electrode on the principal surface 60SA via side surface wiring in place of the through wiring 62H.

Bonding electrodes 61 are disposed on a first side surface 60SS1 of the wiring board 60 and a second side surface 60SS2, which faces the first side surface 60SS1. Electrodes 64, which are bonded to the external electrodes 42 on the rear surface 40SB of the image pickup portion 40, are disposed on the first principal surface 60SA. A drive IC configured to convert the image pickup signal into the drive signal configured to drive the light emitting device 50 and other electric parts (not shown) are mounted on the wiring board 60.

The opto-electric composite cable (hereinafter also referred to as "composite cable") 20 includes the optical fiber 21, which transmits an optical signal, and a plurality of electric cables 22, which each transmit an electric signal. The optical fiber 21 is disposed along a center axis of the composite cable 20, and the electric cables 22 are disposed around the optical fiber 21.

The optical signal is a signal as a result of the conversion of the electric signal outputted by the image pickup portion into light, and the electric signal via each of the electric cables is, for example, a sync signal in accordance with which the image pickup portion 40 operates or an electric power signal supplied to the image pickup portion 40 or the drive IC.

The optical fiber 21 includes, for example, a 50-μm-diameter core configured to transmit an optical signal and a 125-μm-diameter cladding configured to cover an outer circumference of the core. An outer envelope 21A is a protection tube configured to protect the optical fiber 21.

The electric cables 22 (20M) are each a coaxial cable including a core wire 22A configured to transmit an electric signal, an outer envelope 22B configured to cover the core wire 22A, a shielding wire 22C, which is a ground potential wire, and an outer envelope 22D configured to cover the shielding wire 22C, or a single-wire cable. The optical fiber 21 and the plurality of electric cables 22 are further covered with an outer envelope 23 to form a single cable.

A cable holder 30, which is disposed in a position closer to the second principal surface 60SB than to the first principal surface 60SA of the wiring board 60, has a rectangular flat-plate-like shape in a plan view and has a second through hole H30 roughly at a center of the cable holder 30. Out of four side surfaces 30SS, two side surfaces 30SS1 and 30SS2, which face each other, each have a plurality of grooves T30 each having an arcuate cross-sectional shape. In the present embodiment, the cable holder 30 is entirely made of copper, which is an electrically conductive material.

A ferrule (fiber holding portion) 35, which has a first through hole H35 located at a center of the ferrule 35, is inserted into the second through hole H30 of the cable holder 30, and the ferrule 35 is bonded via an electrically conductive member, for example, solder. The ferrule 35, which is made of an electrical conductor, is called a ferrule conductor 35M for convenience The optical fiber 21 is inserted into the first through hole H35 of the ferrule 35. In other words, the optical fiber 21 is indirectly inserted into the second through hole H30 of the cable holder 30. The shape of the second through hole H30 conforms to the outer shape of the ferrule 35.

The cable holder 30 is bonded to the electrical conductor pattern 62 on the second principal surface 60SB of the wiring board 60 in such a way that the second through hole H30 faces the hole portion H60 of the wiring board 60 via an electrically conductive member, for example, solder. The optical fiber 21, when inserted into the first through hole H35 of the ferrule 35, is aligned with the light emitting portion 51 of the light emitting device 50. The optical signal emitted by the light emitting portion 51 enters the optical fiber 21 via the hole portion H60 of the wiring board 60.

On the other hand, the grooves T30 in the cable holder 30 are fixing portions configured to fix the electric cables 22 in such a way that the core wires 22A are disposed on the bonding electrodes 61 on the wiring board 60. The grooves, which are the fixing portions, may instead have a rectangular cross-sectional shape, a V-letter-like shape, or any other shape configured to be capable of fixing the shielding wires 22C.

The cable holder 30 formed of an electrical conductor is called a holder conductor 30M for convenience. The holder conductor 30M formed of inner surfaces of the grooves T30 electrically connects the shielding wires 22C of the plurality of electric cable 22 to each other.

The plurality of shielding wires 22C are electrically connected to the ground potential electrode 42B of the image pickup portion 40 via the holder conductor 30M, the ferrule conductor 35M, the electrical conductor pattern 62 on the wiring board 60, and the through wiring 62H.

The cable holder 30 may instead be so configured that part of a surface of the cable holder 30 is formed of the holder conductor 30M as long as the shielding wires 22C can be connected to the ferrule conductor 35M. The ferrule 35 may also instead be so configured that part of a surface of the ferrule 35 is formed of the ferrule conductor 35M as long as the ferrule conductor 35M can be connected to the ground potential electrode (electrical conductor pattern 62) on the wiring board 60.

An inner diameter of the semicircular grooves T30 is roughly equal to an outer diameter of the shielding wires 22C in the electric cables 22. The shielding wires 22C are bonded to the grooves T30 via an electrically conductive member 39, such as solder. The configuration in which the shielding wires 22C are fixed to the grooves T30 causes the core wires 22A to be positioned on the bonding electrodes 61 on the side surfaces 60SS of the wiring board 60. In other words, the cable holder 30 is a positioning portion (cable aligning portion) configured to specify the arrangement of the plurality of electric cables 22.

As described above, the image pickup portion 40 is driven by using the sync signal and the electric power signal transmitted along the electric cables 22 and outputs an image pickup signal. The image pickup signal outputted by the image pickup portion 40 is converted by the light emitting device 50 into an optical signal. The optical signal is then transmitted via the optical fiber 21 to the light receiving module 10X.

The image pickup signal may instead be converted by an electronic part (not shown) mounted on the wiring board 60 into the drive signal and then inputted to the light emitting device 50. The electronic part is also driven by the electric power signal transmitted along one of the electric cables 22.

The opto-electric composite module 1 disposed in the distal end portion 90A of the endoscope 9 is an ultracompact module dedicated for endoscope having a maximum outer dimension of, for example, 1 mm or smaller in a direction perpendicular to an optical axis O. It is therefore not easy to connect the composite cable 20 to the optical transmission module 10. As already described above, when the plurality of core wires 22A are disposed on and bonded to the respective bonding electrodes 61 on the wiring board 60, in particular, stress is likely to be induced in the optical fiber 21, so that the optical fiber 21 is likely to be damaged.

In the opto-electric composite module 1, however, the optical fiber 21 is fixed via the cable holder 30 before the core wires 22A are bonded. Therefore, for example, when the core wires 22A are bonded, the optical fiber 21 is unlikely to be damaged, whereby the opto-electric composite module 1 is highly reliable. Further, the core wires 22A have been positioned. The opto-electric composite module 1 can therefore be readily manufactured.

Moreover, in the opto-electric composite module 1, the surface of the cable holder 30, which is formed of an electrical conductor, is a holder conductor to which the shielding wires 22C in the plurality of electric cable 22 are bonded via the electrically conductive members 39. Connecting any of the shielding wires 22C to the ground potential electrode 42B of the image pickup portion 40 via the cable holder 30 (holder conductor 30M) and the ferrule 35 (ferrule conductor 35M) eliminates the need for wiring for connection between the shielding wire 22C and the ground potential electrode 42B in the opto-electric composite module 1. Therefore, the opto-electric composite module 1 has a simple structure and is further readily manufactured.

<Method for Manufacturing Opto-Electric Composite Module>

Figure 5:
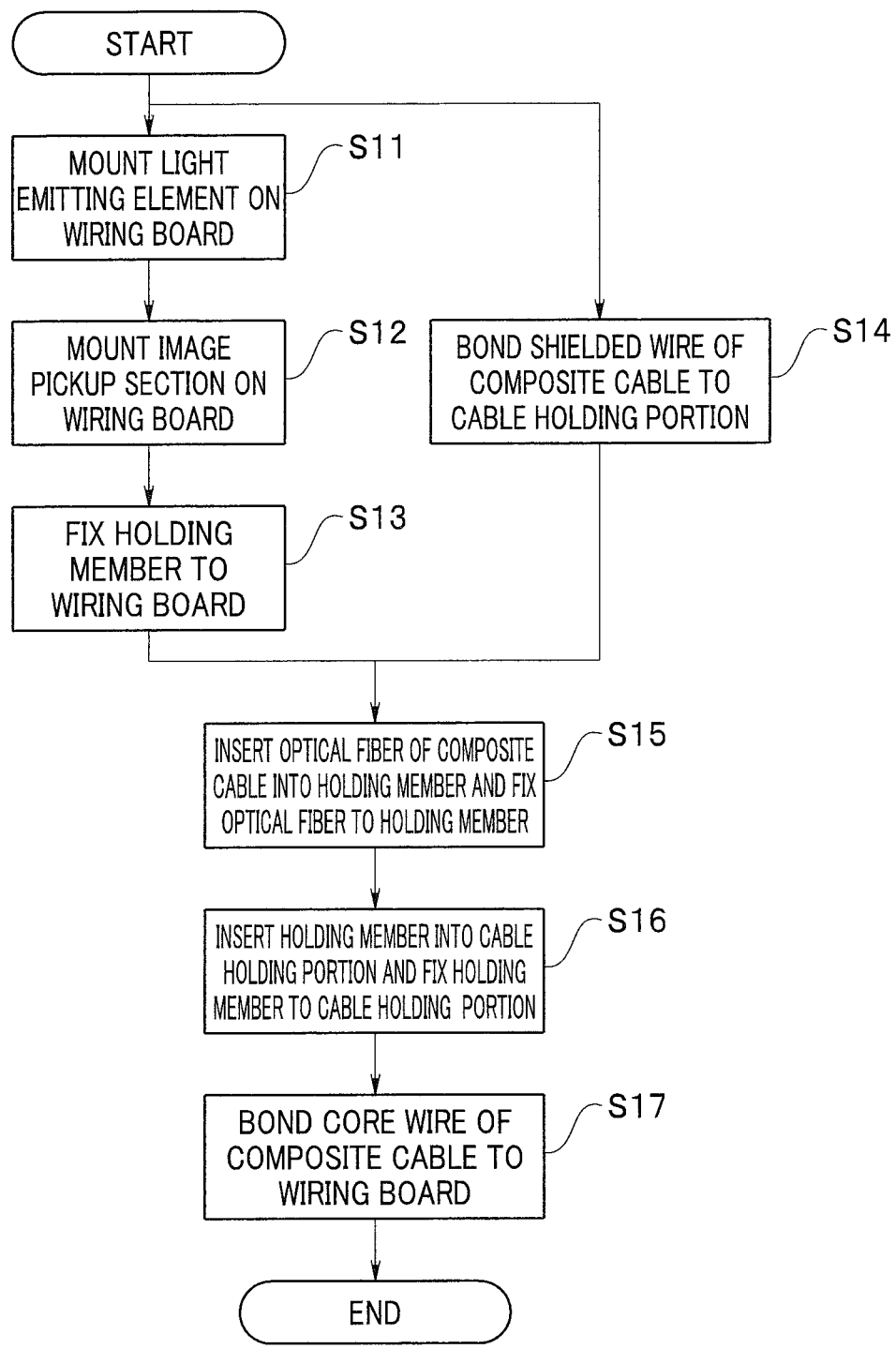
FIG. 5 is a flowchart for describing a method for manufacturing the opto-electric composite module of the endoscope according to the second embodiment.

A method for manufacturing the opto-electric composite module 1 will next be described with reference to the flowchart of FIG. 5.

<Step S11> Mount Light Emitting Device on Wiring Board

The light emitting device 50 is a vertical cavity surface emitting laser (VCSEL). For example, the light emitting device 50, which is an ultracompact module having the dimension of 250 μm×250 μm in the plan view, has the light emitting surface 50SA, on which the light emitting portion 51 having the diameter of 10 μm and the two external electrodes 52, which have the diameter of 50 μm and supply the light emitting portion 51 with the drive signal, are provided.

Figure 6:
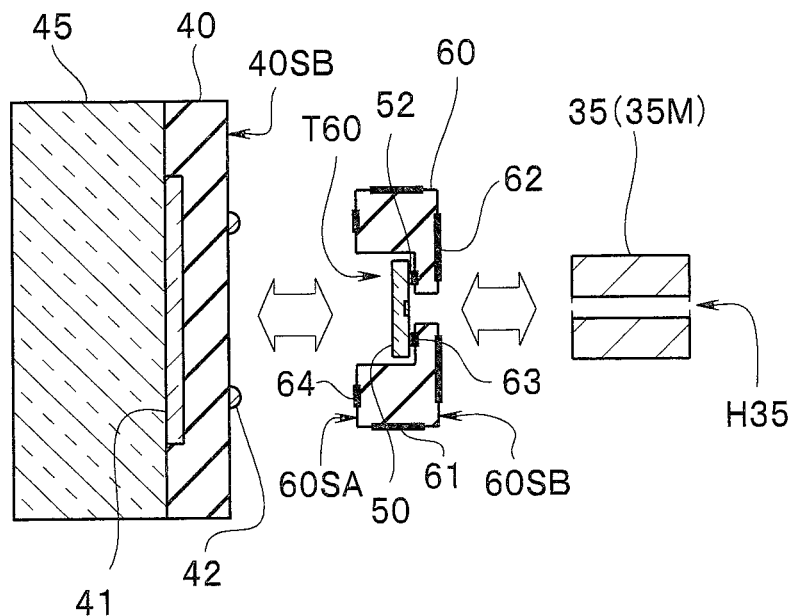
FIG. 6 is a cross-sectional view for describing the method for manufacturing the opto-electric composite module of the endoscope according to the second embodiment.

The base body of the wiring board 60 is made, for example, of a ceramic material, a glass material, a resin material, a fiber reinforced resin material, or silicon. The external electrodes 52 of the light emitting device 50 are bonded to the electrodes 63 on the bottom surface of the recessed portion T60 in the first principal surface 60SA, for example, in an ultrasonic bonding process, as shown in FIG. 6. The depth of the recessed portion T60 is so set that the light emitting device 50, which is mounted in the recessed portion T60, does not protrude out of the recessed portion T60. A plurality of chip parts, such as a chip capacitor, may be mounted on the wiring board 60 as well as the drive IC.

<Step S12> Mount Image Pickup Portion on Wiring Board

The image pickup portion 40 is a complementary metal oxide semiconductor (CMOS) image sensor, a charge coupled device (CCD), or the like. An optical unit formed of a plurality of lenses, filters, optical apertures, and other components may be further disposed on the cover glass plate 45.

The external electrodes 42 on the rear surface 40SB of the image pickup portion 40 are bonded to the electrodes 64 on the first principal surface 60SA of the wiring board 60, as shown in FIG. 6.

<Step S13> Fix Ferrule to Wiring Board

The ferrule 35 made of an electrically conductive material is bonded to a ground potential electrode 62 on the second principal surface 60SB of the wiring board 60 via an electrically conductive material, such as solder, as shown in FIG. 6.

Step S12 may be carried out before step S11. Further, a sleeve 36 (see FIG. 15), which has a through hole for ferrule into which the ferrule 35 is inserted, may be accurately positioned in advance and disposed on the second principal surface 60SB of the wiring board 60.

\<Step S14\> Bond Shielding Wires to Cable Holder

Figure 7:
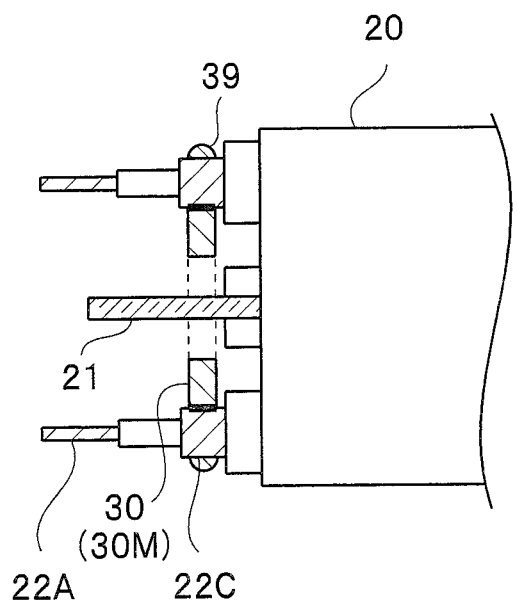
FIG. 7 is a cross-sectional view for describing the method for manufacturing the opto-electric composite module of the endoscope according to the second embodiment.
Figure 8:
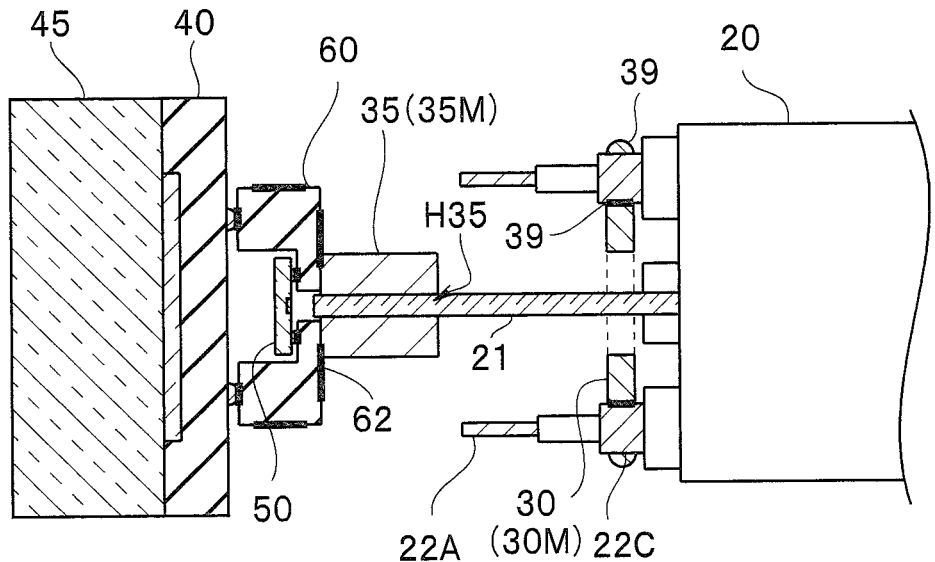
FIG. 8 is a cross-sectional view for describing the method for manufacturing the opto-electric composite module of the endoscope according to the second embodiment.
Figure 9:
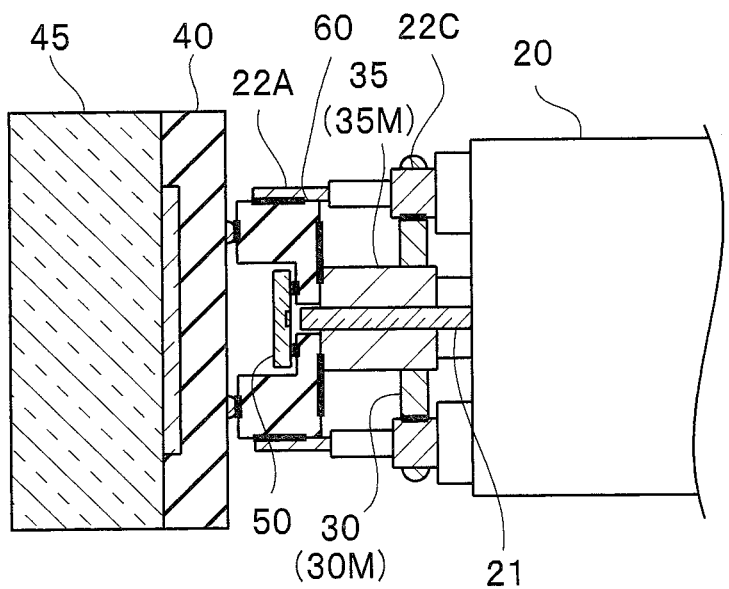
FIG. 9 is a cross-sectional view for describing the method for manufacturing the opto-electric composite module of the endoscope according to the second embodiment.

The shielding wires 22C in the electric cables 22 in the composite cable 20 are bonded and fixed to the grooves T30 in side surfaces of the electrically conductive cable holder 30 via the electrically conductive member 39, such as solder, as shown in FIG. 7. In this process, the plurality of electric cables 22 are so positioned that the core wires 22A in the electric cables 22 are placed on the respective bonding electrodes 61. In FIGS. 7, 8, and 9, the composite cable 20 is drawn in a simplified manner.

The cable holder 30 and the ferrule 35 may be entirely made of an electrically conductive material containing copper, aluminum, iron, gold, or other metal or a metal alloy or may be primarily made of a ceramic or stainless steel material as a base material, and a low-resistance copper plated film as the holder conductor 30M and the ferrule conductor 35M may be placed on a surface of the base material. The cable holder 30 and the ferrule 35 may each instead be an MID.

The cable holder 30 and the ferrule 35 may instead be made of different electrically conductive materials. Still instead, for example, the holder conductor 30M may be an electrically conductive film disposed on only part of a surface of a non-electrically conductive material as long as electrical conduction between the shielding wires 22C and the ground potential electrode 62 can be ensured.

\<Step S15\> Fix Optical Fiber to Ferrule

The optical fiber 21 is inserted into the first through hole H35 of the ferrule 35, as shown in FIG. 8. The optical fiber 21 is so accommodated in the composite cable 20 as to be movable forward and rearward.

The optical fiber 21 is so positioned that the distance between a distal end surface of the optical fiber 21 and the light emitting surface of the light emitting device 50 is a predetermined value and fixed to the ferrule 35 by using a resin adhesive.

\<Step S16\> Fix Ferrule to Cable Holder

The ferrule 35 is inserted into the second through hole H30 of the cable holder 30 and bonded and fixed to the ground potential electrode 62 on the wiring board 60 via solder as shown in FIG. 9. The core wires 22A in the electric cables 22 are then so positioned as to be in contact with the bonding electrodes 61 on the wiring board 60. The shielding wires 22C are electrically connected to the ground potential electrode 42B of the image pickup portion 40 via the holder conductor 30M of the cable holder 30, the ferrule conductor 35M of the ferrule 35, and the ground potential electrode 62 on the wiring board 60.

In other words, the holder conductor 30M is a wiring member configured to connect the shielding wires 22C to the ferrule conductor 35M, and the ferrule conductor 35M is a wiring member configured to connect the holder conductor 30M to the ground potential electrode 62 on the wiring board 60.

\<Step S17\> Bond Core Wires to Wiring Board

The core wires 22A are bonded to the bonding electrode 61 on the wiring board 60. At this point, the plurality of core wires 22A have been so disposed as to be aligned with the positions of the respective bonding electrodes 61. Further, the optical fiber 21 has been inserted into and fixed to the ferrule 35. There is therefore no risk of breakage of the optical fiber 21. The opto-electric composite module 1 is therefore readily manufactured and highly reliable.

Modifications of Second Embodiment

Opto-electric composite modules 1A to 1F of endoscopes 9A to 9F according to modifications of the second embodiment are similar to the opto-electric composite module 1 and provide the same effects as the effects provided by the opto-electric composite module 1, and a component having the same function therefore has the same reference character and will not be described.

Modification 1 of Second Embodiment

Figure 10:
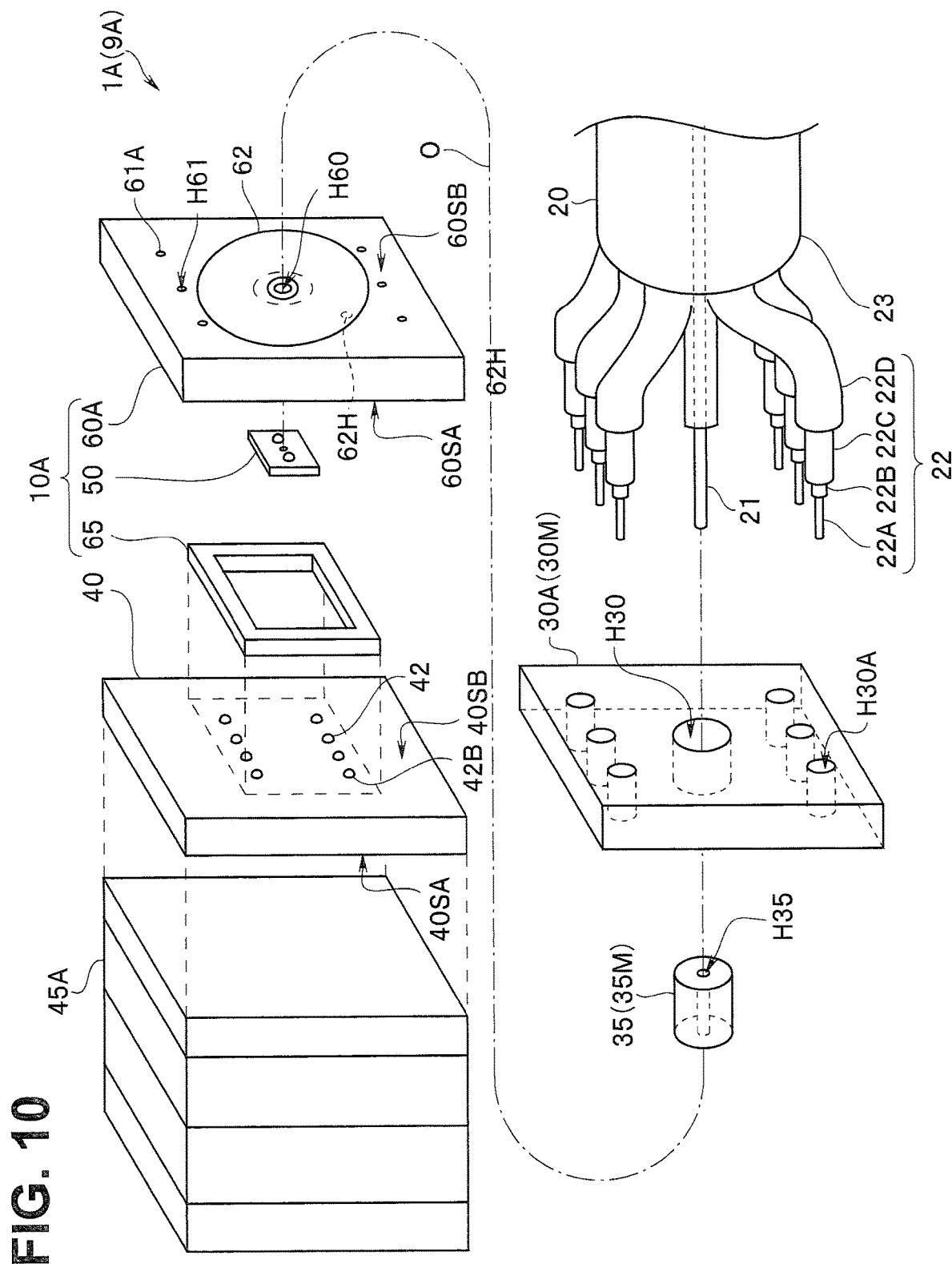
FIG. 10 is an exploded view of an opto-electric composite module of an endoscope according to Modification 1 of the second embodiment.

In the opto-electric composite module 1A of the endoscope 9A according to Modification 1, fixing portions H30A of a cable holder 30A each have an opening that is a circular hole as shown in FIG. 10. The opening of each of the holes, which are the fixing portions, may instead have, for example, a rectangular or polygonal shape.

An inner diameter (inner dimension) of the fixing portions H30A is slightly greater than the outer diameter of the shielding wires 22C in the composite cable 20. The bonding electrodes on a wiring board 60A are each a recessed portion (via) H61 having a bottom. An inner diameter of each of the recessed portions H61 is slightly greater than an outer diameter of the core wires 22A. The fixing portions of the cable holder may each be a hole. The plurality of fixing portions may have different opening shapes. The recessed portions H61, which are the bonding electrodes, may each have no bottom but may each be a through hole.

Further, a frame-shaped spacer 65 is disposed on the first principal surface 60SA of the wiring board 60A. The spacer 65 is provided with wiring (not shown) configured to connect the external electrodes 42 of the image pickup portion 40 to the wiring board 60A. In other words, the recessed portion for accommodating the light emitting device 50 is not an essential portion of the wiring board 60.

A box-shaped laminate optical module 45A, in which a plurality of optical members including a lens, a filter, and a cover glass plate are laminated on each other, is glued to the light receiving surface 40SA of the image pickup portion 40.

Modification 2 of Second Embodiment

Figure 11:
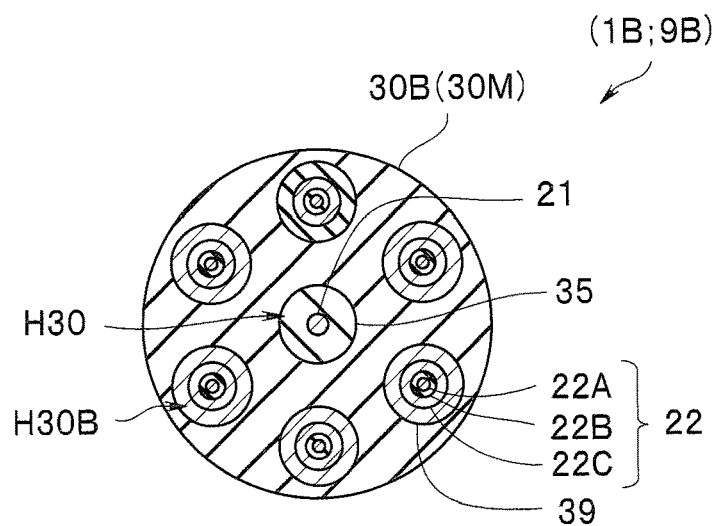
FIG. 11 is a cross-sectional view of an opto-electric composite module of an endoscope according to Modification 2 of the second embodiment.

A cable holder 30B of the opto-electric composite module 1B of the endoscope 9B according to Modification 2 has a disc-like shape, and fixing portions H30B are holes so disposed as to be rotationally symmetric, as shown in FIG. 11. The plurality of shielding wires 22C are inserted into the fixing portions H30B (holder conductors 30M) of the cable holder 30B formed of an electrical conductor and bonded to the fixing portions H30B via the electrically conductive members 39.

In the opto-electric composite module 1B, the arrangement of the plurality of core wires 22A in the cable holder 30B is similar to the arrangement in the composite cable 20, and it is therefore unnecessary to greatly deform the distal end portions of the electric cables 22. The opto-electric composite module 1B is therefore more readily manufactured than the opto-electric composite module 1.

The cable holder in a plan view viewed in the directions perpendicular to the optical axis of the cable holder does not necessarily have a rectangular shape but may have, for example, a circular or polygonal shape.

Modification 3 of Second Embodiment

Figure 12A:
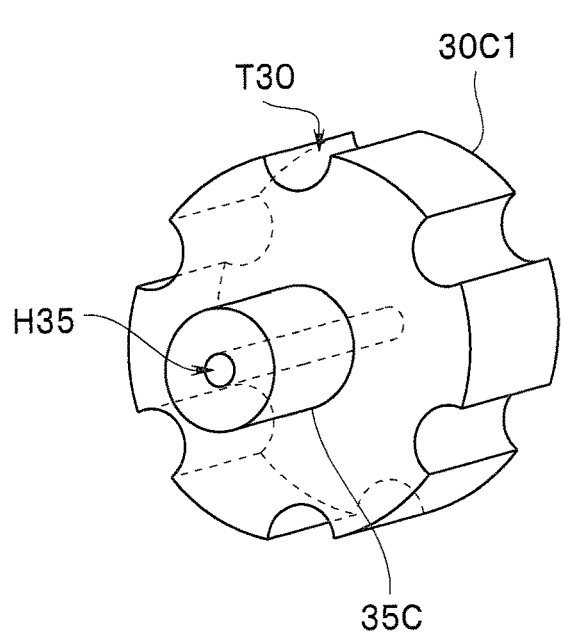
FIG. 12A is a perspective view of a cable holder of an opto-electric composite module of an endoscope according to Modification 3 of the second embodiment.

In the opto-electric composite module 1C of the endoscope 9C according to Modification 3, a cable holder 30C1 is integrated with a ferrule portion having the first through hole H35, as shown in FIG. 12A.

The cable holder 30C1 is made, for example, of an MID, and electrodes (holder conductors) on the inner surfaces of the grooves T30 in the side surface of the cable holder 30C1 are connected, for example, to electrodes (ferrule conductors) on a ferrule portion and electrically connected to the ground potential electrode 42B of the image pickup portion 40. The holder conductors and the ferrule conductors may be formed of a one-piece electrical conductor.

Since the cable holder 30C1 is integrated with the ferrule portion, the opto-electric composite module 1C is more readily manufactured than the opto-electric composite module 1.

Figure 12B:
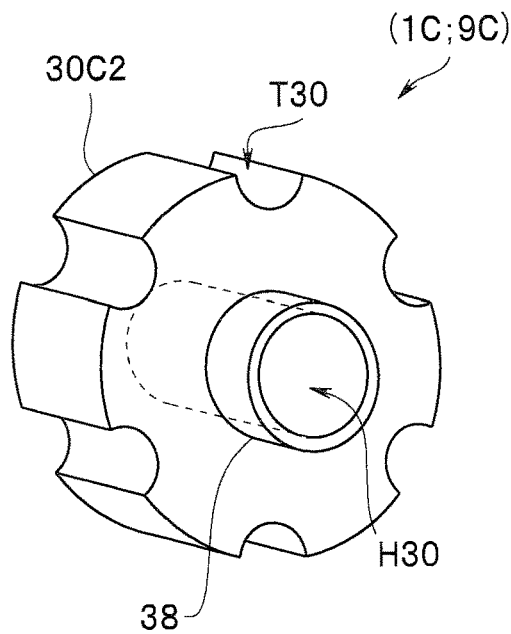
FIG. 12B is a perspective view of a cable holder of an opto-electric composite module of an endoscope according to Modification 3 of the second embodiment.

Further, a cable holder 30C2 shown in FIG. 12B has a protruding portion 38, which extends from the second through hole H30. The protruding portion 38 that comes into contact with the second principal surface 60SB of the wiring board 60 specifies the distance between the cable holder 30C2 and the wiring board 60.

Modification 4 of Second Embodiment

Figure 13:
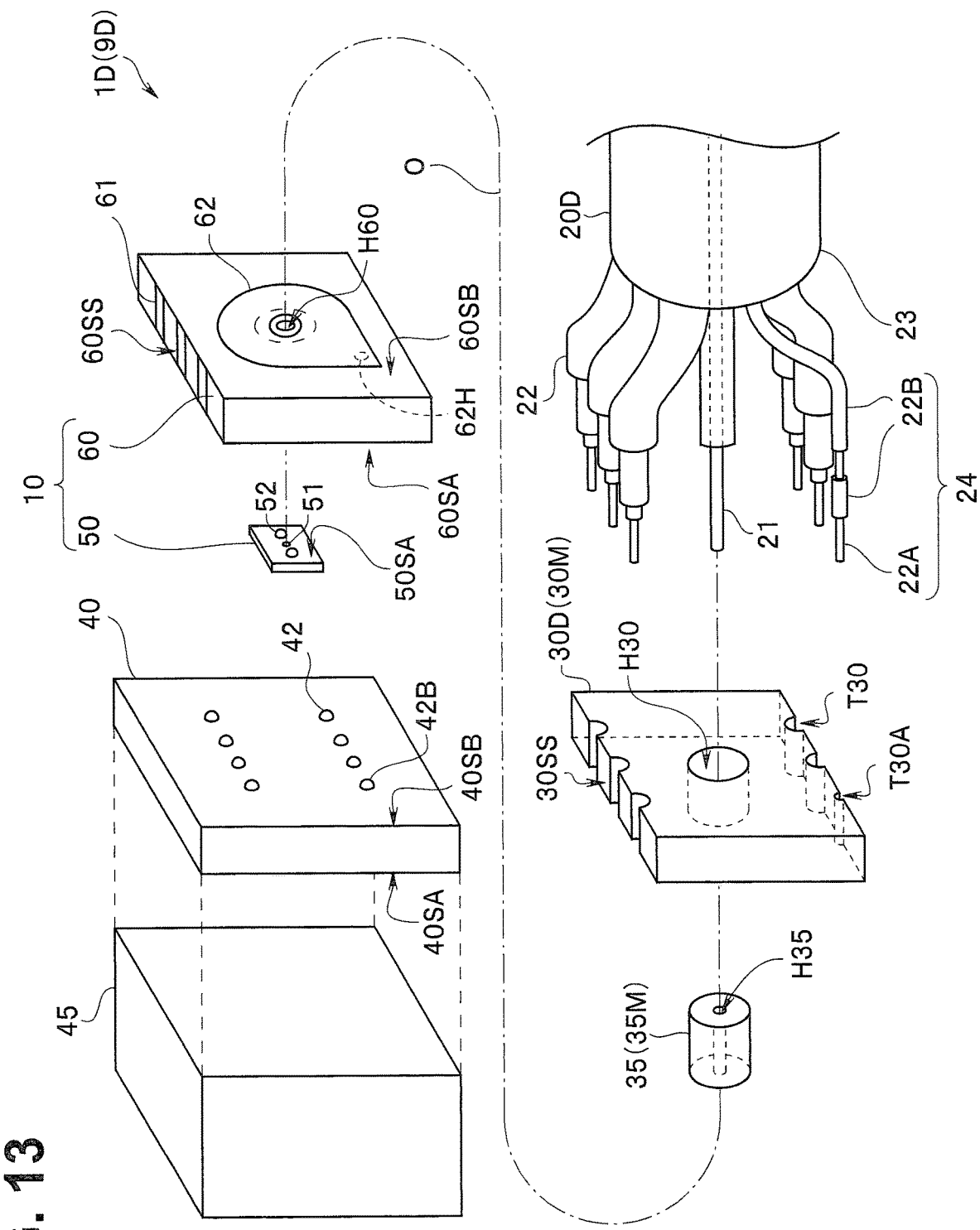
FIG. 13 is an exploded view of an opto-electric composite module of an endoscope according to Modification 4 of the second embodiment.

A plurality of electric cables in the opto-electric composite module 1D of the endoscope 9D according to Modification 4 include a ground electric cable 24, in which the core wire is a ground potential core wire 22A, as shown in FIG. 13. The ground electric cable 24 is a single-wire electric cable in which the core wire 22A is covered with the outer envelope 22B, and the core wire 22A is bonded to an inner surface of a groove T30A, which is a fixing portion, of a cable holder 30D via an electrically conductive member, such as solder. The core wire of the single-wire cable may be one element wire or a twisted wire formed of a plurality of wires twisted around one another.

An inner diameter of the groove T30A, which has a semicircular cross-sectional shape, is slightly greater than the outer diameter of the core wire 22A but smaller than the inner diameter of the grooves T30, which are the other fixing portions. The core wire 22A is also connected to the ground potential electrode (not shown) out of the plurality of bonding electrodes 61 on the side surfaces 60SS of the wiring board 60. To prevent a short circuit due to contact with another cable, the outer envelope 22B of the ground electric cable 24 is partially peeled off.

The cable holder 30D is connected to the wiring board 60 via the core wires 22A. Therefore, in the opto-electric composite module 1D, the shielding wires and the core wires 22A are not necessarily connected to each other entirely via the electrically conductive ferrule 35 as long as the ferrule conductor 35M connects the shielding wires and the core wires 22A to each other, and a non-electrically conductive ferrule can be used. The electrically conductive ferrule 35 may, of course, also be used in the opto-electric composite module 1D. Any of the core wires in the plurality of shielded electric cables may be the ground potential core wire.

Modification 5 of Second Embodiment

Figure 14:
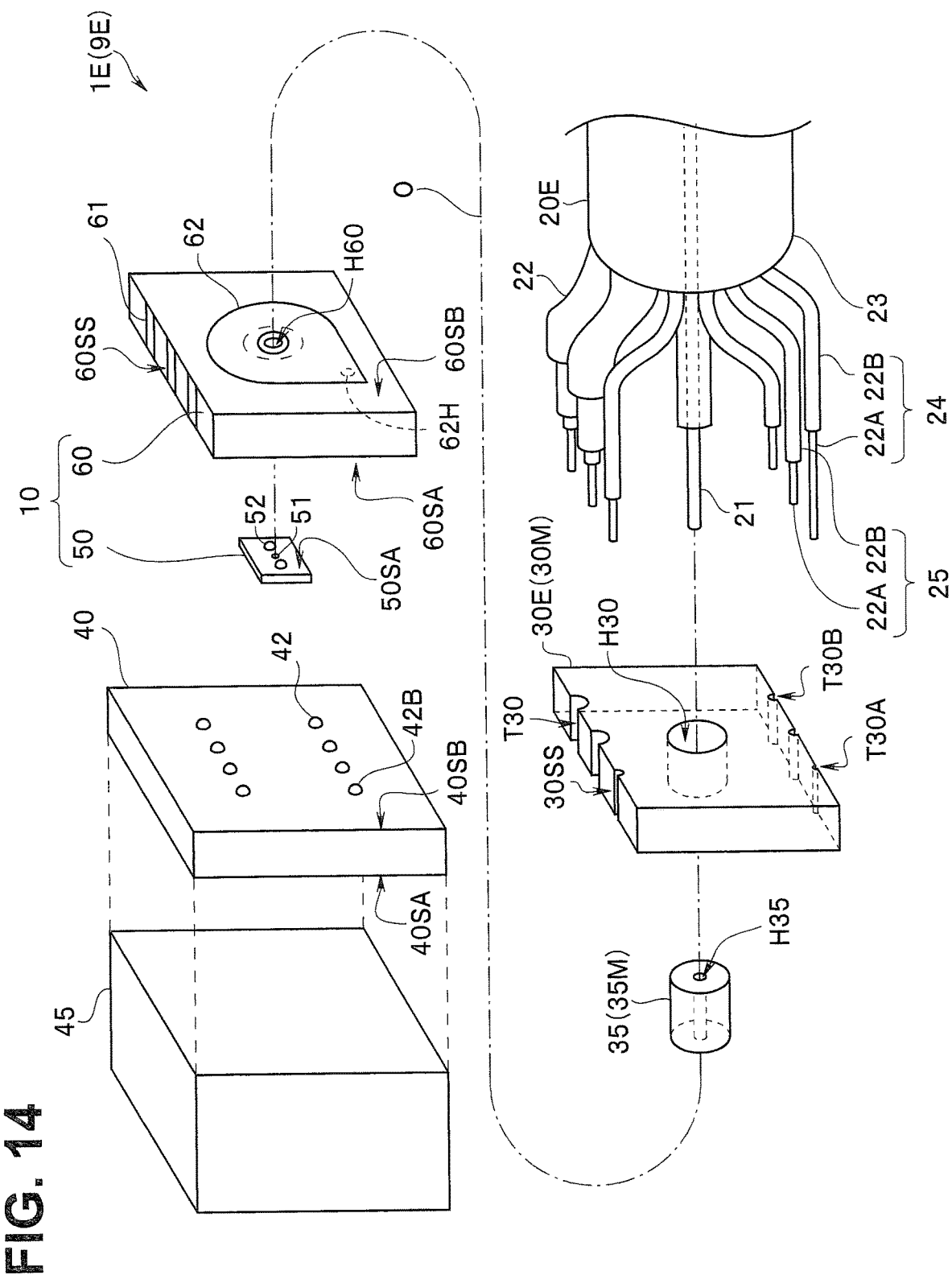
FIG. 14 is an exploded view of an opto-electric composite module of an endoscope according to Modification 5 of the second embodiment.

A plurality of electric cables in the opto-electric composite module 1E of the endoscope 9E according to Modification 5 includes shielded electric cables 22, the ground electric cable 24, and a single-wire electric cable 25, as shown in FIG. 14.

The core wire 22A of the ground electric cable 24 is connected to the ground potential electrode (wiring pattern 62) on the wiring board 60 via a fixing portion of an electrically conductive cable holder 30E (holder conductor 30M) and the ferrule 35 (ferrule conductor 35M).

On the other hand, the single-wire electric cable 25 is, for example, a power source cable configured to supply electric power. The core wire 22A, which is an electric power supply wire, of the single-wire electric cable 25 is bonded to a bonding electrode 61. In the case of the single-wire electric cable 25, the outer envelope 22B, which covers the core wire 22A, is fixed to a groove T30B, which is a fixing portion, of the cable holder 30E, for example, via an adhesive. An inner diameter of the groove T30B is slightly greater than an outer diameter of the outer envelope 22B. In other words, the cable holder 30E has three types of grooves having different inner diameters, T30, T30A, and T30B, in the side surfaces 30SS.

The core wire 22A of the single-wire electric cable 25 may be thicker than the core wires 22A of the electric cables 22, which are each a coaxial cable. Further, the plurality of electric cables in the opto-electric composite module 1E may include the shielded electric cables 22 and the single-wire electric cable 25 but no ground electric cable 24.

Modification 6 of Second Embodiment

Figure 15:
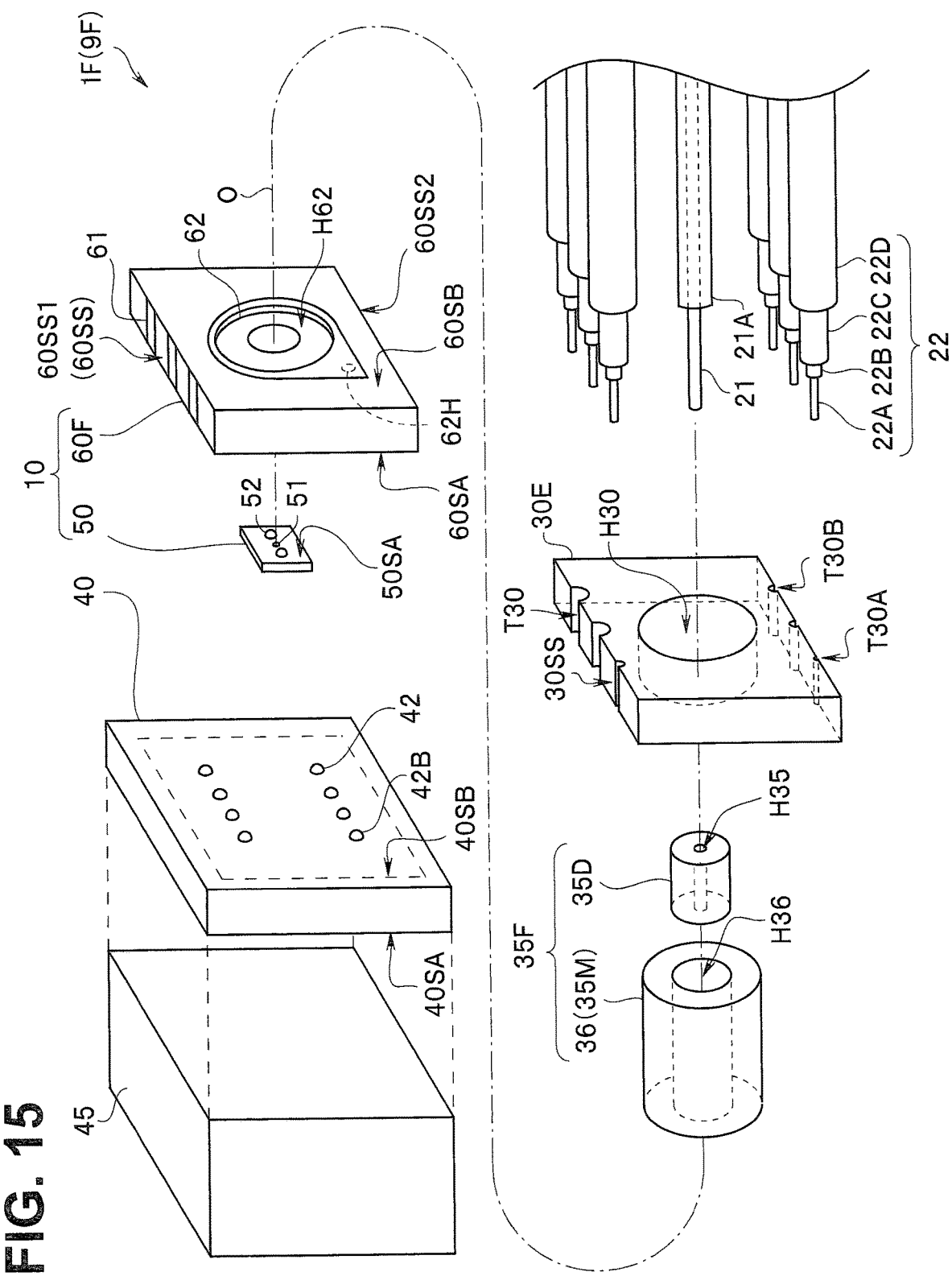
FIG. 15 is an exploded view of an opto-electric composite module of an endoscope according to Modification 6 of the second embodiment.

In an opto-electric composite module 1F of an endoscope 9F according to Modification 6, a ferrule 35F includes a ferrule main body 35D, which has the first through hole H35, and the sleeve 36, which has a through hole H36 for ferrule into which the ferrule main body 35D is inserted as shown in FIG. 15.

In the case of the ferrule 35F, the sleeve 36 formed of an electrical conductor is the ferrule conductor 35M. The ferrule main body 35D may be a non-electrical conductor. Only part of a surface of the sleeve 36 may be an electrical conductor.

A wiring board 60F having a base body made of glass has a recessed portion H62 in the second principal surface 60SB, and the recessed portion H62 has a shape into which the sleeve 36 fits. Since the wiring board 60F is transparent, no hole portion that serves as the optical path is provided. The wiring board 60F having the recessed portion H62 allows the sleeve 36, that is, the ferrule 35F to be readily positioned.

Also in the other embodiments, a recessed portion for positioning the sleeve 36 or the ferrule 35 is preferably formed in the second principal surface of the wiring board.

The optical fiber 21 or the electric cables 22 do not each form an opto-electric composite cable. Also in the opto-electric composite modules 1 and 1A to 1E, the optical fiber 21 or the electric cables 22 may not each form an opto-electric composite cable.

The opto-electric composite module 1F, in which the optical fiber 21 fixed to the ferrule main body 35D is inserted into the sleeve 36, is readily manufactured.

Third Embodiment

An opto-electric composite module 1G of an endoscope 9G according to a third embodiment is similar to the opto-electric composite module 1 of the endoscope 9 and others and provide the same effects as the effects provided by the opto-electric composite module 1 and others, and a component having the same function therefore has the same reference character and will not be described.

The opto-electric composite module 1G differs from the opto-electric composite module 1 and others in that no cable holder is provided. In other words, the endoscope 9G includes the opto-electric composite module 1G, which is disposed in the distal end portion 90A of the insertion portion 90 and converts an electric signal into an optical signal, the optical fiber 21 inserted through the insertion portion 90 and which transmits the optical signal, and the electric cables 22 inserted through the insertion portion 90 and which include the core wires 22A and the shielding wires 22C.

Figure 16:
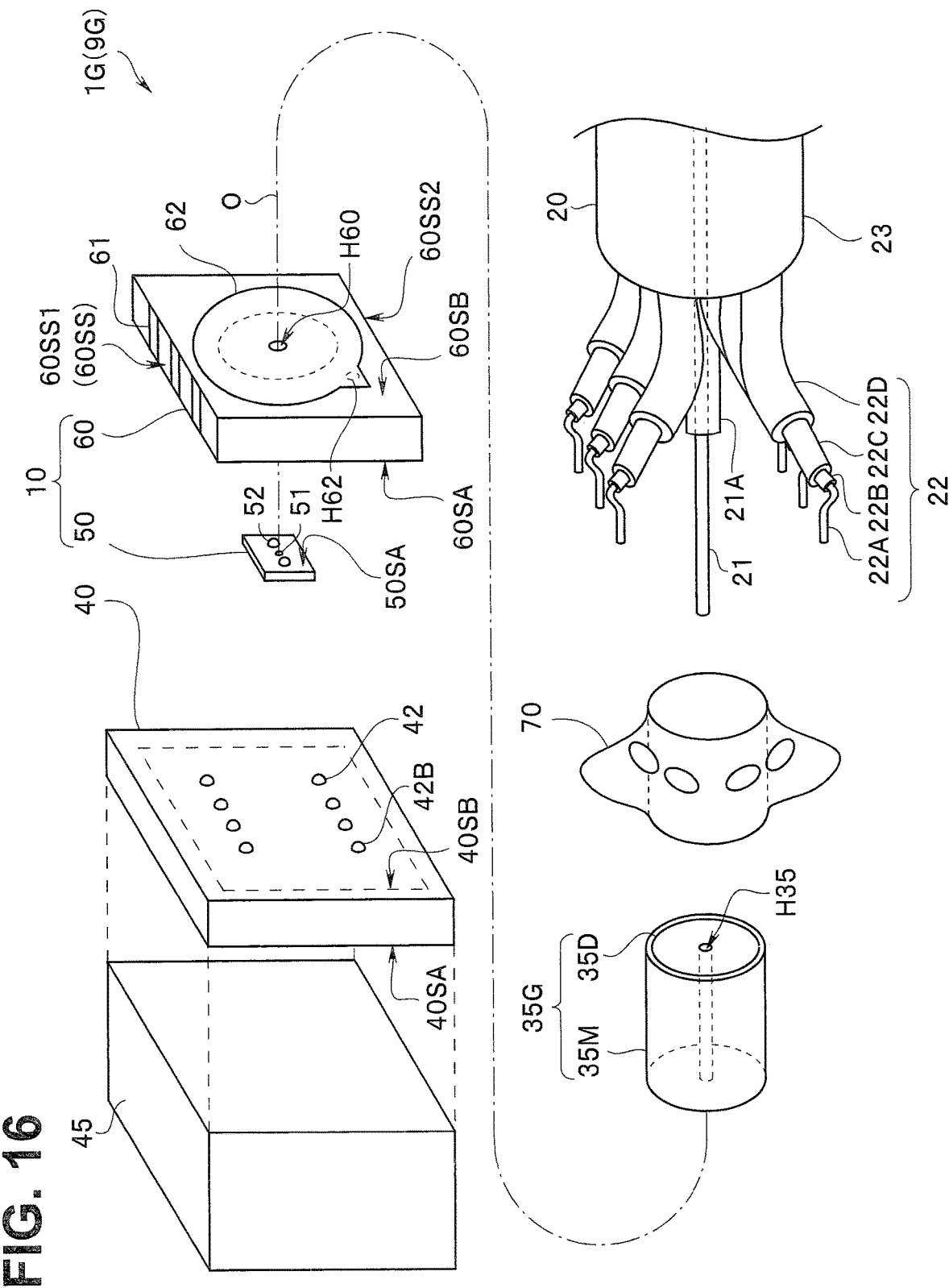
FIG. 16 is an exploded view of an opto-electric composite module of an endoscope according a third embodiment.
Figure 17:
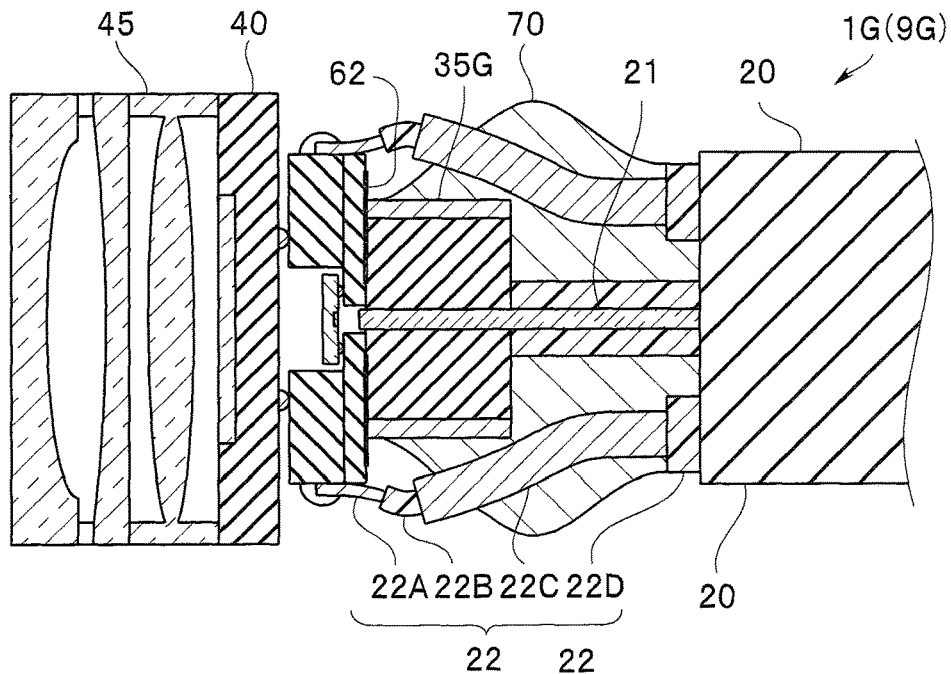
FIG. 17 is a cross-sectional view of the opto-electric composite module of the endoscope according to the third embodiment.
Figure 18:
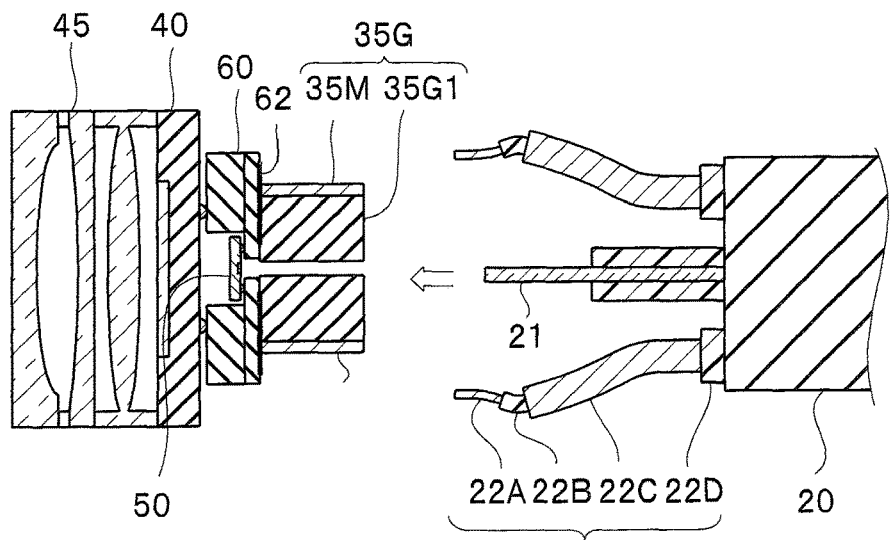
FIG. 18 is a cross-sectional view for describing a method for manufacturing the opto-electric composite module of the endoscope according to the third embodiment.

The opto-electric composite module 1G includes the light emitting device 50, which converts the electric signal outputted by the image pickup portion 40 into an optical signal, the wiring board 60, which has the first principal surface 60SA and the second principal surface 60SB, which faces the first principal surface 60SA, and includes the light emitting device 50 mounted on the first principal surface 60SA and to which the core wires 22A are bonded, and a ferrule 35G, which has the first through hole 1135, into which a distal end portion of the optical fiber 21 is inserted, as shown in FIGS. 16 to 18.

In the case of the ferrule 35G, an outer circumferential surface of the ferrule 35G is the ferrule conductor 35M electrically connected to the ground potential electrode 42B of the image pickup portion 40, as shown in FIG. 17. In other words, the ferrule 35G includes the ferrule conductor 35M on the outer circumferential surface of a ferrule 35G1 formed of a non-electrical conductor. The electrically conductive ferrule 35 can, of course, also be used in the opto-electric composite module 1G.

The plurality of shielding wires 22C in the electric cables 22 are bonded to the ferrule 35 via an electrically conductive member 70, for example, solder.

In other words, the ferrule 35 is bonded to the electrical conductor pattern 62 on the second principal surface 60SB of the wiring board 60, for example, via solder. The electrical conductor pattern 62 is electrically connected to an electrode (not shown) on the first principal surface 60SA via through wiring 62H. The electrode on the first principal surface 60SA is bonded to the ground potential electrode 42B of the image pickup portion 40.

The plurality of shielding wires 22C are connected to the ground potential electrode 42B of the image pickup portion 40 via the electrically conductive member 70, the ferrule conductor 35M, the electrical conductor pattern 62 on the wiring board 60, and the through wiring 62H.

On the other hand, the core wires 22A are connected to the external electrodes 42 of the image pickup portion 40 via the bonding electrodes 61 on the side surfaces of the wiring board 60.

As described above, the connection between the plurality of shielding wires 22C and the ferrule conductor 35M can be collectively made via the electrically conductive member 70.

The opto-electric composite module 1G requires no wiring for connecting the shielding wires 22C to the ground potential electrode 42B. The opto-electric composite module 1G therefore has a simple structure and can be readily manufactured.

Modifications of Third Embodiment

Opto-electric composite modules 1H and 1I of endoscopes 914 and 91 according to modifications of the third embodiment are similar to the opto-electric composite module 1G and others and provide the same effects as the effects provided by the opto-electric composite module 1G and others, and a component having the same function therefore has the same reference character and will not be described.

Modification 1 of Third Embodiment

Figure 19:
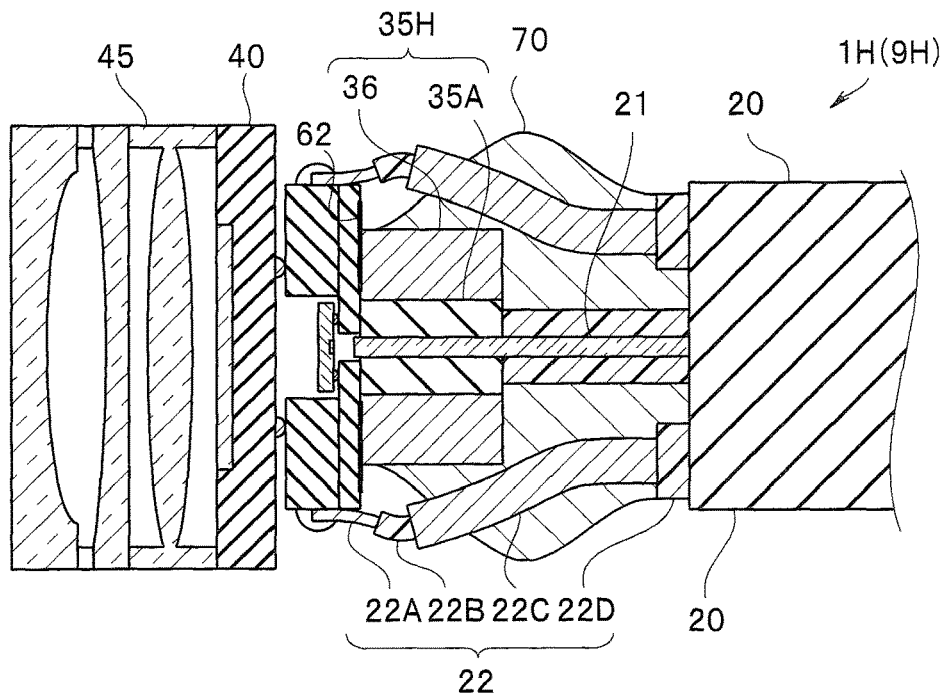
FIG. 19 is a cross-sectional view of an opto-electric composite module of an endoscope according to Modification 1 of the third embodiment.

In the opto-electric composite module 1H of the endoscope 9H according to Modification 1 of the third embodiment, a ferrule 35E1 includes a ferrule main body 35A, which has the first through hole H35, and the sleeve 36, into which the ferrule main body 35A is inserted, as does the opto-electric composite module 1F, as shown in FIG. 19.

The ferrule main body 35A may be formed of an electrical conductor or a non-electrical conductor. The sleeve 36 is the ferrule conductor 35M, which is fanned of an electrical conductor. An electrical conductor film that is the ferrule conductor 35M may be disposed on a surface of the sleeve 36 made of a non-electrical conductor.

The plurality of shielding wires 22C are connected to the ground potential electrode 42B of the image pickup portion 40 via the electrically conductive member 70, the ferrule conductor 35M, the electrical conductor pattern 62 on the wiring board 60, and the through wiring 62H.

The opto-electric composite module 1H, in which the optical fiber 21 fixed to the ferrule main body 35A is inserted into the sleeve 36, is readily manufactured.

Modification 2 of Third Embodiment

Figure 20:
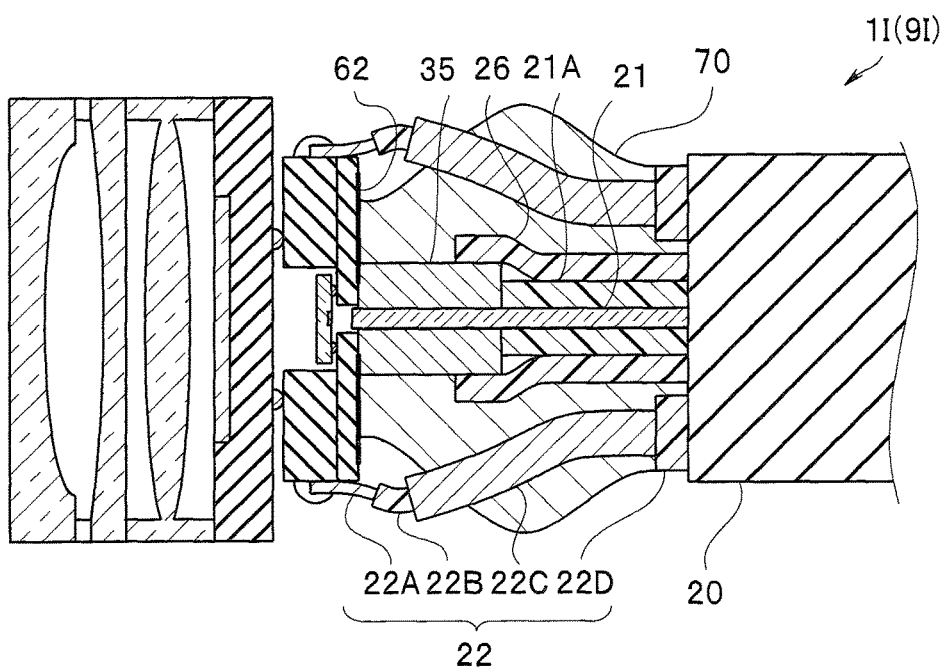
FIG. 20 is a cross-sectional view of an opto-electric composite module of an endoscope according to Modification 2 of the third embodiment.

In the opto-electric composite module 1I of the endoscope 9I according to Modification 2 of the third embodiment, a rear portion of the distal end portion of the optical fiber 21 is covered with a protection tube 26, which prevents the optical fiber 21 from being in contact with the electrically conductive member 70, as shown in FIG. 20. Further, a distal end portion of the protection tube 26 fits into a surface of a rear end portion of the ferrule 35. The protection tube 26 is made, for example, of a PEEK resin.

The protection tube 26 that fits into the ferrule 35 allows the optical fiber 21 to be stably held and prevents the electrically conductive member 70 from causing an adverse effect, for example, no stress distribution.

The outer envelope 21A prevents the rear portion of the distal end portion of the optical fiber 21 from being in contact with the electrically conductive member 70 also in the opto-electric composite module 1I. The outer envelope 21A prevents the electrically conductive member 70 from causing an adverse effect, for example, no stress distribution on the optical fiber 21. The rear portion of the distal end portion of the optical fiber 21 may instead be so covered with an electrically conductive film as not to be in contact with the electrically conductive member 70.

The present invention is not limited to the embodiments, the modifications, and the like described above, and a variety of changes, combinations, and applications are possible to the extent that the changes, combinations, and applications do not depart from the substance of the present invention.

What is claimed is:

1. An endoscope comprising:
   an insertion portion;
   an opto-electric composite module disposed in a distal end portion of the insertion portion and configured to convert an electric signal into an optical signal;
   an optical fiber inserted through the insertion portion and configured to transmit the optical signal; and
   a plurality of electric cables inserted through the insertion portion, each of the plurality of electric cables comprising a core wire and a shielding wire,
   wherein the opto-electric composite module comprises:
      an image pickup sensor;
      a light emitting device configured to convert the electric signal outputted by the image pickup sensor into the optical signal;

a wiring board having a first principal surface and a second principal surface, with the light emitting device mounted on the first principal surface, and including a plurality of bonding electrodes to which the plurality of core wires are bonded, respectively;

a ferrule having a first through hole, with the optical fiber inserted into the first through hole optically coupled to the light emitting device; and a cable holder having one of a plurality of grooves or holes to which the plurality of core wires are fixed, with the plurality of core wires disposed in positions where the plurality of core wires are bonded to the plurality of respective bonding electrodes, the cable holder being disposed in a position closer to the second principal surface than to the first principal surface of the wiring board, wherein a surface of each of the plurality of grooves or a surface of each of the plurality of holes is a holder conductor electrically connected to a ground potential electrode of the image pickup sensor, and the shielding wires are bonded to the holder conductor of the cable holder via an electrically conductive member.

2. The endoscope according to claim 1, wherein a surface of the ferrule is a ferrule conductor electrically connected to the ground potential electrode, and the holder conductor is electrically connected to the ground potential electrode via the ferrule conductor.

3. The endoscope according to claim 1, wherein the cable holder is integrated with the ferrule.

4. The endoscope according to claim 1, wherein the ferrule includes a ferrule main body having the first through hole and a sleeve into which the ferrule main body is inserted.

5. The endoscope according to claim 1, wherein any of the plurality of core wires is a ground potential core wire, and the ground potential core wire is bonded to the holder conductor via an electrically conductive member.

6. The endoscope according to claim 1, wherein the optical fiber and the electric cables form an opto-electric composite cable.

7. The endoscope according to claim 1, wherein any of the plurality of core wires is a single-wire cable having an outer envelope configured to cover the core wire, and the single-wire cable is an electric power supplying wire configured to supply electric power, and the outer envelope is bonded to the groove or the hole.

8. An insertion section for use with an endoscope, the insertion section comprising:

an opto-electric composite module disposed in a distal end portion of the insertion portion and configured to convert an electric signal into an optical signal;

an optical fiber inserted through the insertion portion and configured to transmit the optical signal; and a plurality of electric cables inserted through the insertion portion, each of the plurality of electric cables comprising a core wire and a shielding wire, wherein the opto-electric composite module comprises:

an image pickup sensor;

a light emitting device configured to convert the electric signal outputted by the image pickup sensor into the optical signal;

a wiring board having a first principal surface and a second principal surface, with the light emitting device mounted on the first principal surface, and including a plurality of bonding electrodes to which the plurality of core wires are bonded, respectively;

a ferrule having a first through hole, with the optical fiber inserted into the first through hole optically coupled to the light emitting device; and a cable holder having one of a plurality of grooves or holes to which the plurality of core wires are fixed, with the plurality of core wires disposed in positions where the plurality of core wires are bonded to the plurality of respective bonding electrodes, the cable holder being disposed in a position closer to the second principal surface than to the first principal surface of the wiring board, wherein a surface of each of the plurality of grooves or a surface of each of the plurality of holes is a holder conductor electrically connected to a ground potential electrode of the image pickup sensor, and the shielding wires are bonded to the holder conductor of the cable holder via an electrically conductive member.

* * * * *